US009302407B2

(12) United States Patent  (10) Patent No.: US 9,302,407 B2
Gruber  (45) Date of Patent: Apr. 5, 2016

(54) FACILITY FOR REPAIRING FLAWS IN PIECES OF WOOD

(71) Applicant: Gruber Automations GmbH, Mettmach (AT)

(72) Inventor: Josef Gruber, Mettmach (AT)

(73) Assignee: Gruber Automations GmbH, Mettmach (AT)

( * ) Notice: Subject to any disclaimer, the term of this patent is extended or adjusted under 35 U.S.C. 154(b) by 0 days.

(21) Appl. No.: 14/459,918

(22) Filed: Aug. 14, 2014

(65) Prior Publication Data

US 2015/0047948 A1  Feb. 19, 2015

(30) Foreign Application Priority Data

Aug. 19, 2013 (AT) ............................... A 50514/2013

(51) Int. Cl.
*B27G 1/00* (2006.01)
*B65G 47/84* (2006.01)
*G01N 21/898* (2006.01)
(52) U.S. Cl.
CPC ................ *B27G 1/00* (2013.01); *B65G 47/846* (2013.01); *G01N 21/8986* (2013.01)
(58) Field of Classification Search
CPC .............................. B27G 1/00; G01N 21/8986
See application file for complete search history.

(56) References Cited

U.S. PATENT DOCUMENTS

| 4,763,703 | A | * | 8/1988 | Fromm | ................ | B23D 45/146 |
| | | | | | | 144/2.1 |
| 4,984,172 | A | * | 1/1991 | Luminari | ................ | B27G 1/00 |
| | | | | | | 144/332 |
| 5,014,501 | A | * | 5/1991 | Constantin | ................ | B65B 7/20 |
| | | | | | | 53/173 |
| 5,377,815 | A | * | 1/1995 | Vetter | ................ | B65G 47/847 |
| | | | | | | 198/476.1 |
| 2003/0178586 | A1 | | 9/2003 | Hubert et al. | | |
| 2007/0034297 | A1 | * | 2/2007 | Zielke | ................ | B23D 59/008 |
| | | | | | | 144/392 |
| 2010/0154934 | A1 | * | 6/2010 | Hatch, Jr. | ................ | B27C 9/04 |
| | | | | | | 144/363 |
| 2012/0186700 | A1 | * | 7/2012 | Tolonen | ............ | G01N 21/8986 |
| | | | | | | 144/402 |

FOREIGN PATENT DOCUMENTS

| AT | 397 368 B | 3/1994 |
| AT | 11 042 U2 | 3/2010 |
| AT | 507 776 A4 | 8/2010 |
| DE | 20 2007 005 516 U1 | 5/2008 |
| DE | 202007005516 | * 6/2008 ............... B27G 1/00 |
| EP | 2 424 715 B1 | 3/2013 |

* cited by examiner

*Primary Examiner* — Gene Crawford
*Assistant Examiner* — Thomas Randazzo
(74) *Attorney, Agent, or Firm* — Collard & Roe, P.C.

(57) ABSTRACT

A facility for repairing flaws in pieces of wood (3) has a device (13) for recognizing and surveying the flaws, has a conveyor device (1), which receives the pieces of wood (3) to be repaired in a manner correct for processing, and has tools, which are displaceable in multiple axes in relation to the pieces of wood (3) on the conveyor device (1), for repairing the flaws. To ensure advantageous design conditions, the conveyor device (1) forms a collar, which revolves about at least one vertical axis, made of receptacle segments (2) which hold the pieces of wood (3) in a vertical processing location, and the receptacle segments (2) are provided with the tools, which are displaceable in multiple axes, for repairing the flaws.

4 Claims, 3 Drawing Sheets

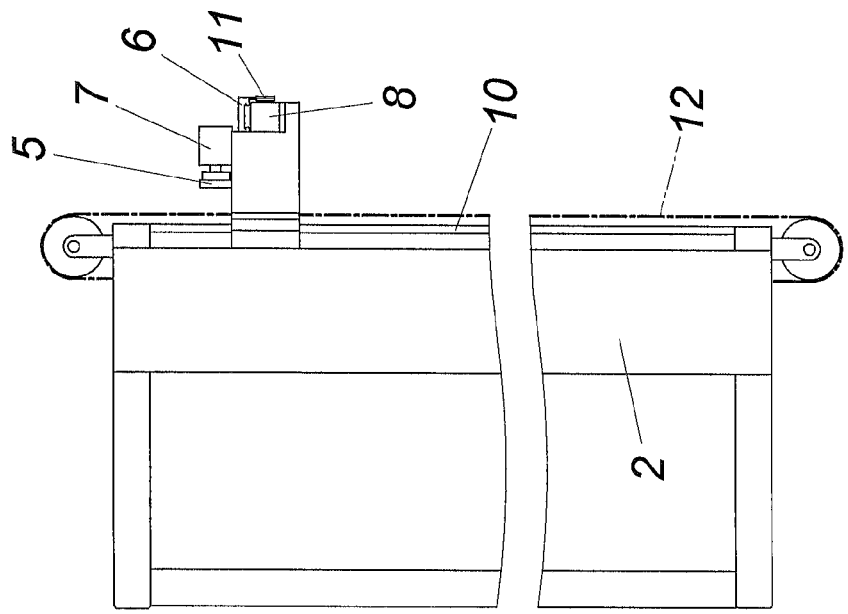
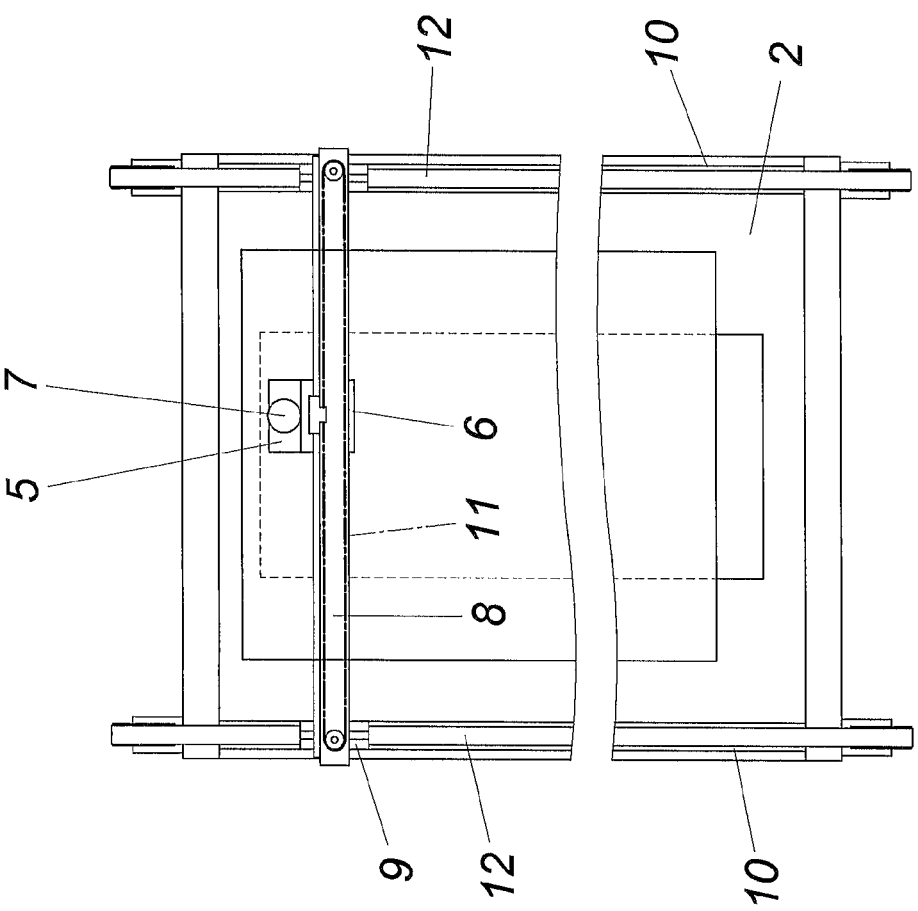

FACILITY FOR REPAIRING FLAWS IN PIECES OF WOOD

CROSS REFERENCE TO RELATED APPLICATIONS

Applicant claims priority under 35 U.S.C. §119 of Austrian Application No. A50514/2013 filed Aug. 19, 2013, the disclosure of which is incorporated by reference.

BACKGROUND OF THE INVENTION

1. Field of the Invention

The invention relates to a facility for repairing flaws in pieces of wood having a device for recognizing and surveying the flaws, having a conveyor device, which receives the pieces of wood to be repaired in a manner correct for processing, and having tools, which are displaceable in multiple axes in relation to the pieces of wood on the conveyor device, for repairing the flaws.

2. Description of the Related Art

To be able to repair flaws in wood, such as cracks, knot holes, resin galls, and the like, by machine, holding the wood to be repaired on a conveyor device in a manner correct for processing, to which guides parallel to the conveyor direction for longitudinal carriages are assigned on both sides, the longitudinal carriages bearing guides extending transversely to the conveyor direction for a transverse carriage, which in turn receives a tool carriage, which is displaceable perpendicularly to the longitudinal and transverse carriages, for approach of the respective tool to the wood, is known (AT 11 042 U2). The tool carriages can therefore be displaced in accordance with the location coordinates, which are measured via a surveying device, of the established flaws of the wood to be processed and the flaws can be repaired with the aid of the tools provided for this purpose, wherein the provision of longitudinal carriages on both sides of the conveyor device substantially shortens the processing time for the wood to be repaired because of the doubling thus possible of the tools usable independently of one another.

In order that the flaws of the piece of wood can be repaired during its longitudinal conveyance on a conveyor device, providing a fixed gantry, which spans the conveyor device, and on which at least one transverse carriage is mounted, which forms a guide extending in the conveyor direction of the conveyor device for a tool carriage which can approach, is additionally known (EP 2 424 715 B1). The tool can accordingly be aligned via the transverse carriage and the tool carriage in relation to the flaw to be processed of a piece of wood clamped on the conveyor device and can also be moved with the conveyor movement of the wood along the guide, which extends in the conveyor direction, for the tool carriage.

These known facilities for repairing flaws in pieces of wood have the disadvantage above all that in the case of the conveyance after a simultaneous processing of multiple pieces of wood clamped in succession on the conveyor device, the structural length of the facility is enlarged at least to the sum of the lengths of the receptacles provided on the conveyor device for the pieces of wood to be processed simultaneously. In addition, the wood having the most flaws determines the processing time for all other pieces of wood, which possibly require shorter processing times.

SUMMARY OF THE INVENTION

The invention is therefore based on the object of embodying a facility for repairing flaws in pieces of wood so that the structural length required for the simultaneous processing of multiple pieces of wood is shortened and the processing time of the pieces of wood having a predefined average number of flaws can be selected independently of the processing time, which is required for repairing a number of flaws which exceeds the average number.

Proceeding from a facility of the type described at the outset, the invention achieves the stated object in that the conveyor device forms a collar, which revolves about at least one vertical axis, made of receptacle segments, which hold the pieces of wood to be repaired in a vertical processing location, and the receptacle segments are provided with the tools, which are displaceable in multiple axes, for repairing the flaws.

Due to the implementation of the conveyor device in the form of a collar, which revolves about at least one vertical axis, made of receptacle segments, which each receive at least one piece of wood to be repaired in a vertical processing location, which is parallel to the revolution axis, it is firstly possible to substantially shorten the structural length of the facility in spite of the simultaneous processing of multiple pieces of wood clamped in succession in the conveyor direction, without having to accept impairment of the processing. On the contrary, due to the assignment of the tools required in each case for repairing the detected flaws to the individual receptacle segments, a processing station results in the region of each receptacle segment, which can be operated completely independently from the processing stations formed by the remaining receptacle segments, and which enables the repair of all flaws of the respective piece of wood without re-clamping it. The wood processing can be performed in this case both during the conveyor movement of the conveyor device and also while it is stationary, so that dead times in this regard may be avoided. In addition, the number of the receptacle segments and the tools assigned to the receptacle segments can be adapted to one another in dependence on an average number of flaws per piece of wood so that the flaws corresponding to an average number can be repaired during one revolution of the conveyor device. If the average number of flaws is exceeded in a case, such a piece of wood thus does require a longer processing time, but neither the dwell time of the remaining pieces of wood to be repaired in the conveyor device nor the conveyor speed thereof are thus affected, because the excess flaws can be repaired during a further revolution of the piece of wood.

The recognition and surveying of the flaws could be performed before the application of the pieces of wood to be repaired to the conveyor device, however, with the difficulty that not only the coordinates of the flaws in relation to the wood, but rather also those of the wood in relation to the receptacle segment must be detected. The location detection of the pieces of wood becomes superfluous due to the detection of the flaws in the location, which is correct for processing, of the pieces of wood on the receptacle segments. It is therefore recommended that the conveyor device be driven step-by-step in accordance with the segment division and the device for recognizing and surveying the flaws be assigned to the receptacle segments in at least one of the rotational positions, which are determined by the step-by-step operation and are successively assumed by the receptacle segments, so that the flaws of the pieces of wood, which were preferably clamped previously to a conveyor step, can be surveyed in relation to the receptacle segment, to be able to activate the tool carriages in accordance with the measured flaw coordinates and repair the flaws. The individual receptacle segments can advantageously be operated via a loading and unloading apparatus, which ensures the clamping in a manner correct for processing of the pieces of wood to be processed on the individual receptacle segments and the removal of the pieces of wood which are held fixed in location on the receptacle segments during the entire processing cycle.

Although the idea of the invention only relates to moving the receptacle segments with the associated tools in a horizontal revolution path and processing the vertically clamped pieces of wood at the same time, particularly favorable design conditions result if the conveyor device forms a rotor having the receptacle segments and therefore the receptacle segments are moved along a circular path. Guides, which are otherwise necessary for the receptacle segments, which are connected to one another like a chain, are dispensed with by the provision of a rotor drivable about a vertical axis.

For the processing of the flaws of the pieces of wood held in a manner correct for processing on the receptacle segments, it is only necessary to guide the tool carriages in multiple axes, to be able to approach the respective flaw coordinates. To be able to ensure simple design conditions in this context, the individual receptacle segments can have lateral vertical guides for longitudinal carriages, which form horizontal guides for transverse carriages, in which tool carriages, which can be applied perpendicularly to the vertical and horizontal guides, are mounted. The vertical guides of the longitudinal carriages and the horizontal guides of the transverse carriages therefore define a Cartesian coordinate system, which is parallel to the receiving of the pieces of wood in the receptacle segments, having a coordinate axis perpendicular to these guides for the tool carriages.

BRIEF DESCRIPTION OF THE DRAWINGS

The object of the invention is illustrated as an example in the drawing. In the figures:

FIG. 3 shows a receptacle segment of the facility according to FIGS. 1 and 2 in a front view in a larger scale, and FIG. 4 shows the receptacle segment according to FIG. 3 in a side view, also in a larger scale.

DETAILED DESCRIPTION OF PREFERRED EMBODIMENTS

Figure 1:
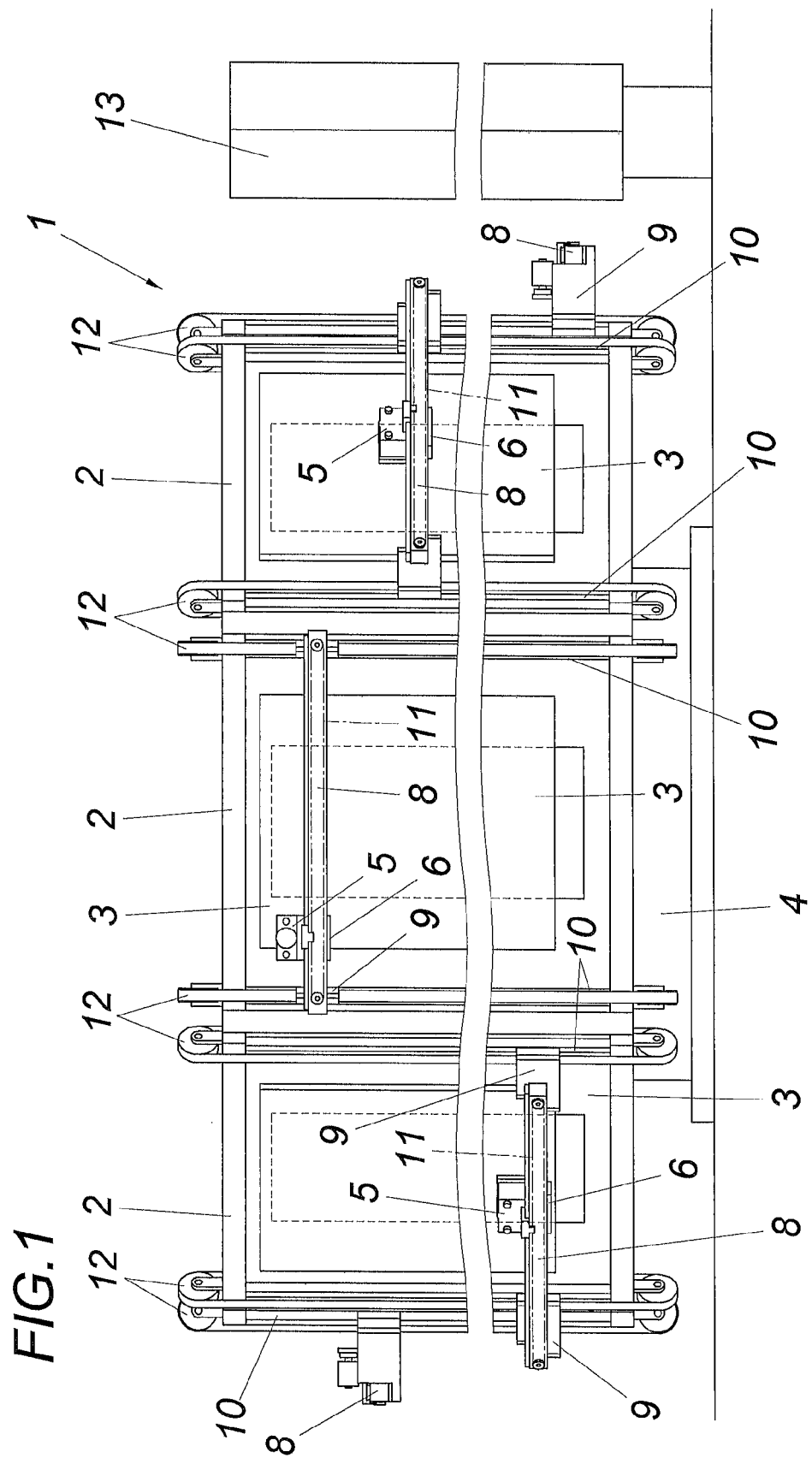
FIG. 1 shows a facility according to the invention for repairing flaws in pieces of wood in a schematic side view.
Figure 2:
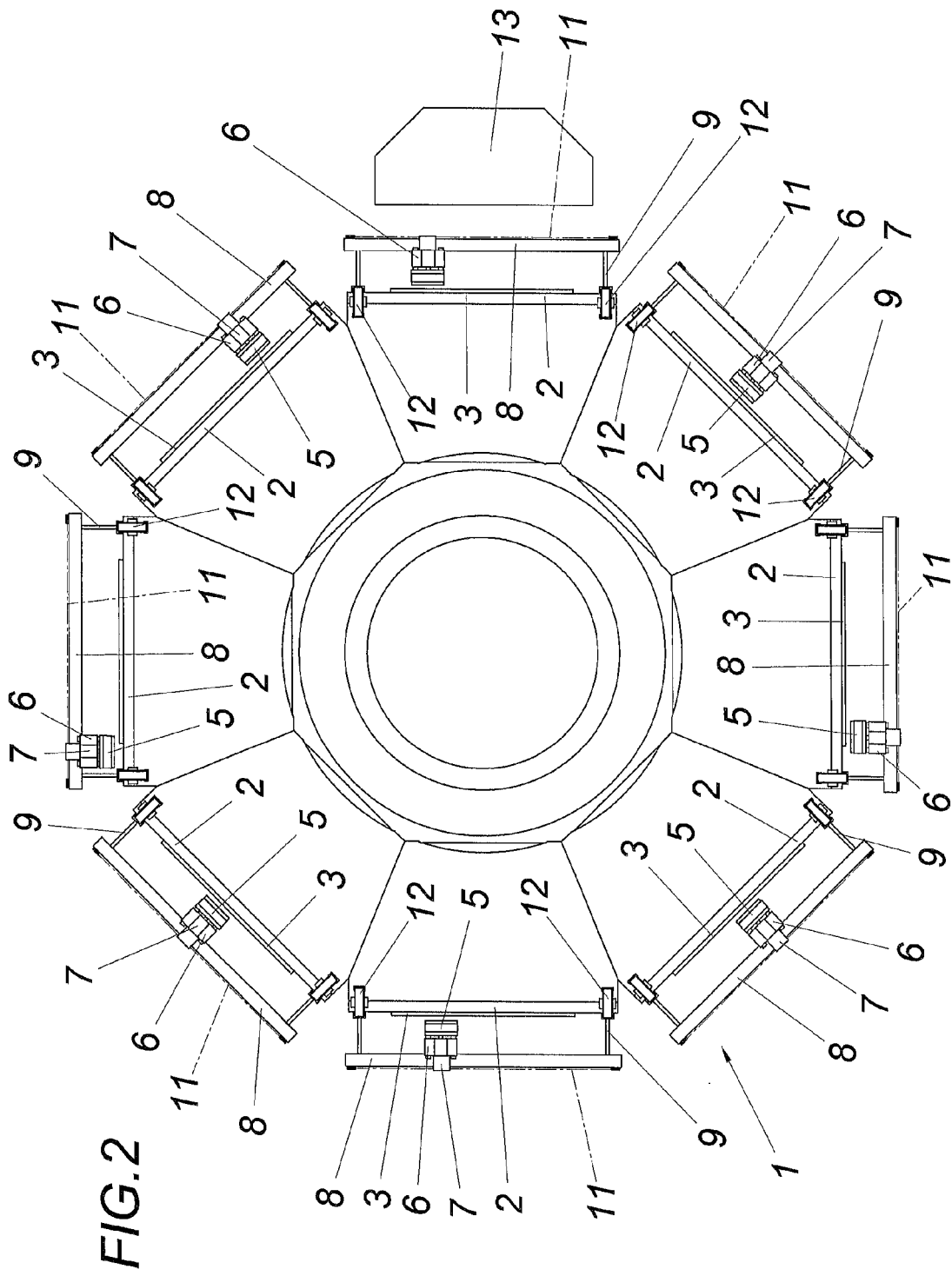
FIG. 2 shows this facility in a simplified top view in a smaller scale.

The illustrated facility for repairing flaws in pieces of wood has a conveyor device 1 made of a collar of receptacle segments 2 for the pieces of wood 3 to be processed, which are held in a conventional manner clamped in a vertical location in a manner correct for processing on the individual receptacle segments 2. According to the exemplary embodiment, the conveyor device 1 forms a rotor comprising the receptacle segments 2, which can be driven to revolve step-by-step about a vertical axis. The rotary bearing 4 receiving the rotor is indicated in FIG. 1.

Each of the receptacle segments 2 is assigned at least one tool carriage 5, which is displaceable in multiple axes, and which is provided in a manner known per se with corresponding tools for repairing flaws in the pieces of wood 3. The tool carriages 5 are mounted on a transverse carriage 6 with the aid of a positioning cylinder 7 so they can approach the pieces of wood 3 perpendicularly to the vertical spanning surface of the receptacle segments 2. The transverse carriage 6 is movable along the horizontal guide 8 of a longitudinal carriage 9, which can be displaced along a vertical guide 10 on both sides of the spanning surface of the receptacle segments 2. The positioning drives 11 and 12 for the transverse carriages 6 and the longitudinal carriages 9 are implemented in the exemplary embodiment as belt drives, but this is in no way required.

The rotor forming the conveyor device 1 is driven via a motor (not shown for reasons of clarity) step-by-step in accordance with the segment division, so that the individual receptacle segments 2 successively assume corresponding rotational positions after each conveyance step. Therefore, a device 13 for recognizing and surveying the flaws of the pieces of wood 3 to be process can be assigned to one of these rotational positions, which is preferably clamped on the respective receptacle segment 2 in the rotational position of the conveyor device 1 upstream in the rotational direction of the device 13, after the already processed piece of wood 3 was removed from this receptacle segment 2. As a result of the recognition and surveying of the flaws of the respective pieces of wood 3 clamped on the individual receptacle segments, the longitudinal carriages 9 and the transverse carriages 6, the guides 10, 8 of which define a Cartesian coordinate system parallel to the clamping surface of the receptacle segments 2, can be displaced in accordance with the location coordinates of the determined flaws so that the respective tools used can be approached via the tool carriages 5 to repair the flaws. The processing of the individual pieces of wood 3 occurs during one revolution of the conveyor device 1, wherein stationary times of the conveyor device 1 do not represent dead times for the wood processing, because the individual receptacle segments 2 each form a workstation, in which the complete processing of a piece of wood 3 can be performed. This means, inter alia, that in the case of a larger number of flaws in a piece of wood 3, this piece of wood 3 can be completely processed in a second revolution, but also in only a further partial revolution of the conveyor device 1, wherein the conveyance speed of the conveyor device 1 is maintained, so that the pieces of wood 3 processed in one revolution of the conveyor device 1 do not experience any delay in their processing. The rotational direction of the conveyor device 1 can be reversed in this case in accordance with the respective requirements.

What is claimed is:

1. An apparatus for repairing flaws in pieces of wood, the apparatus comprising:
   (a) a device for recognizing and surveying the flaws;
   (b) a conveyor device receiving the pieces of wood to be repaired in a manner correct for processing; and
   (c) a plurality of tools for repairing the flaws and displaceable in multiple axes in relation to the pieces of wood on the conveyor device;
   wherein the conveyor device forms a collar of receptacle segments holding the pieces of wood to be repaired in a respective vertical processing location and revolving about at least one vertical axis; and
   wherein the receptacle segments are provided with the tools.

2. The apparatus according to claim 1, wherein the conveyor device is drivable step-by-step in accordance with the receptacle segments so that the receptacle segments assume a number of successive rotational positions; and
   wherein the device for recognizing and surveying the flaws is opposite to the receptacle segments in at least one of the rotational positions.

3. The apparatus according to claim 1, wherein the conveyor device forms a rotor having the receptacle segments.

4. The apparatus according to claim 1, wherein each receptacle has lateral vertical guides for longitudinal carriages forming horizontal guides for transverse carriages; and wherein tool carriages are mounted on the transverse carriages so as to be movable in directions perpendicular to the vertical guides and to the horizontal guides.

\* \* \* \* \*